(12) United States Patent
Slessarev et al.

(10) Patent No.: US 8,459,258 B2
(45) Date of Patent: Jun. 11, 2013

(54) METHOD AND APPARATUS TO ATTAIN AND MAINTAIN TARGET END TIDAL GAS CONCENTRATIONS

(75) Inventors: Marat Slessarev, Toronto (CA); Joe Fisher, Thornhill (CA); George Volgyesi, Toronto (CA); Eitan Prisman, Toronto (CA); David Mikulus, Oakville (CA); Chris Hudson, Waterloo (CA); Cliff Ansel, Thornhill (CA)

(73) Assignee: Thornhill Scientific Inc., Toronto (CA)

( * ) Notice: Subject to any disclaimer, the term of this patent is extended or adjusted under 35 U.S.C. 154(b) by 1065 days.

(21) Appl. No.: 11/997,100

(22) PCT Filed: Jul. 28, 2006

(86) PCT No.: PCT/CA2006/001258
§ 371 (c)(1),
(2), (4) Date: Jan. 9, 2009

(87) PCT Pub. No.: WO2007/012197
PCT Pub. Date: Feb. 1, 2007

(65) Prior Publication Data
US 2009/0120435 A1 May 14, 2009

(30) Foreign Application Priority Data
Jul. 28, 2005 (WO) ................ PCT/CA2005/001166

(51) Int. Cl.
*A61M 15/00* (2006.01)
*A61M 16/00* (2006.01)
*F16K 11/00* (2006.01)
*F16K 31/02* (2006.01)
*G05D 11/02* (2006.01)

(52) U.S. Cl.
USPC ............ 128/203.25; 128/203.14; 128/204.21; 128/204.22

(58) Field of Classification Search
USPC ............. 128/200.24, 203.25, 204.23, 205.11, 128/203.12, 203.14, 204.21, 205.12, 205.27, 128/204.22
See application file for complete search history.

(56) References Cited

U.S. PATENT DOCUMENTS 5,320,093 A   6/1994   Raemer
5,647,345 A   7/1997   Saul
(Continued)

FOREIGN PATENT DOCUMENTS

| | | |
|---|---|---|
| CA | 2269890 | 10/2000 |
| WO | WO 03/092776 | 11/2003 |
| WO | WO 2004/073482 | 9/2004 |

OTHER PUBLICATIONS

Vesely et al., "MRI Mapping of Cerebrovascular Reactivity Using Square Wave Changes in End-Todal PCO2", Magnetic Resonance in Medicine, May 23, 2001, 45:1011-1013, Wiley-Liss.

*Primary Examiner* — Kristen Matter
*Assistant Examiner* — Peter S Vasat
(74) *Attorney, Agent, or Firm* — Klein, O'Neill & Singh, LLP

(57) ABSTRACT

In a first aspect, the invention relates to an apparatus for inducing or maintaining a target end tidal concentration of a gas in a subject comprising a breathing circuit, a source of gas flow into the circuit, means for controlling the rate of the source of gas flow into the circuit and means for controlling the concentration of gases in the source gas flow independently from each other. In another aspect, the invention relates to a method of preparing an apparatus for inducing or maintaining a target end tidal concentration of a gas X in a subject comprising selecting a rate of a source gas flow into a breathing circuit, selecting the concentration of at least one constituent gas of a component gas making up the source gas to a level corresponding to the end tidal concentration of the gas X, whereby the apparatus is adapted to administer a source gas having a first gas composition.

21 Claims, 6 Drawing Sheets

U.S. PATENT DOCUMENTS

| | | |
|---|---|---|
| 5,878,744 A * | 3/1999 | Pfeiffer .................... 128/204.23 |
| 5,957,129 A | 9/1999 | Tham et al. |
| 6,536,429 B1 | 3/2003 | Pavlov et al. |
| 6,622,725 B1 * | 9/2003 | Fisher et al. ............. 128/204.21 |
| 2002/0185129 A1 | 12/2002 | Fisher et al. |
| 2004/0060560 A1 | 4/2004 | Stenzler et al. |
| 2004/0144383 A1 | 7/2004 | Thomas et al. |
| 2004/0206354 A1 | 10/2004 | Fisher et al. |
| 2004/0230113 A1 | 11/2004 | Bolam et al. |

* cited by examiner

METHOD AND APPARATUS TO ATTAIN AND MAINTAIN TARGET END TIDAL GAS CONCENTRATIONS

CROSS-REFERENCE TO RELATED APPLICATIONS

This application is a national phase filing, under 35 U.S.C. §371(c), of International Application No. PCT/CA2006/001258, filed Jul. 28, 2006, the disclosure of which is incorporated herein by reference in its entirety, which application claims the benefit, under 35 U.S.C. §119(e), of co-pending PCT Application No. PCT/CA2005/001166, filed Jul. 28, 2005, the disclosure of which is incorporated in its entirety.

FIELD OF THE INVENTION

The invention disclosed herein relates to the field of blood gas control.

BACKGROUND OF THE INVENTION

Ordinarily, when minute ventilation increases, the partial pressure of end tidal $CO_2$ ($P_{ET}CO_2$) decreases and partial pressure of end tidal $O_2$ ($P_{ET}O_2$) increases. U.S. Pat. No. 6,622,725, (Fisher et al.), describes fixing fresh gas flowing into a partial rebreathing circuit, which in that instance was also a sequential gas delivery circuit, in order to maintain constant $P_{ET}CO_2$ in the face of increases in minute ventilation on the part of the subject. Canadian Patent Application 2,346,517 (Fisher et al.) also describes means of keeping $P_{ET}O_2$ constant at a given attained level despite increases in minute ventilation. None of these documents disclose means to set gas flows and gas concentrations into a circuit to attain a target end tidal fractional concentration of $CO_2$ ($F_TETCO2$) and/or a target end tidal fractional concentration of $O_2$ ($F_TETO_2$) for a given minute ventilation ($\dot{V}_E$), that is different from initial $F_TETCO_2$ and $F_TETO_2$.

Providing a level of control that permits attaining a target end tidal fractional concentration of $CO_2$ ($F_TETCO_2$) and/or a target end tidal fractional concentration of $O_2$ ($F_TETO_2$) for a given minute ventilation ($\dot{V}_E$), that is different from initial $F_TETCO_2$ and $F_TETO_2$.can be used for a number of applications. For example, one such application is measuring cerebrovascular reactivity. Cerebral blood flow (CBF) is closely regulated by metabolic demands of the brain tissue. CBF also responds to changes in arterial $PCO_2$ and $PO_2$. The extent of the change in CBF in response to a stimulus is termed cerebrovascular reactivity (CVR). CVR may be a sensitive indicator of abnormal vessels such as vascular dysplasia or tissue abnormalities such as brain swelling and cancer. Quantitatively mapping CVR throughout the brain using imaging techniques such as magnetic resonance imaging (MRI) could identify areas of abnormal CVR.

Brain blood vessel diameter responds to changes in blood $PO_2$ as well as blood $PCO_2$. Blood $PO_2$ and blood $PCO_2$ are strongly tied to end tidal concentrations of $O_2$ and $CO_2$ respectively. Present methods of inducing high $P_{ET}CO_2$ control $P_{ET}O_2$ poorly and do not control $PCO_2$ and $PO_2$ independently.

There are several current methods that are known for changing blood $PCO_2$ and $PO_2$ via control of the gas concentrations in the lungs.

A: Breath-holding

One method for inducing changes in $PCO_2$ during Magnetic Resonance Imaging (MRI) is breath-holding. As there is a rapid drift in the baseline MRI signal, changes in MRI signal resulting from changes in brain blood flow can be detected only by rapidly alternating the stimulus between "control" and "test" values. With respect to $PCO_2$, this requires rapid step changes in $PCO_2$, preferably maintaining $PO_2$ constant. Cycle times of 3 min have been reported by Vesely et al (1) to be suitable, but shorter cycle times would be preferred. Breath-holding induces an increase in $PCO_2$ but it is not well suited to measuring CVR. The rise in blood $PCO_2$ during breath-holding is very slow as it is dependent on body $CO_2$ production ($\dot{V}CO_2$), which is small compared to body capacitance for $CO_2$. During breath holding, alveolar $PO_2$ declines progressively. As $CO_2$ production, $CO_2$ capacitance and the tolerable breath-holding time varies from subject to subject, so will the final blood $PCO_2$ and $P_{ET}O_2$. As there is no gas sampling during breath-holding the blood $PCO_2$ and $PO_2$ is unknown for the duration of the breath-hold so it is not possible to relate the MRI signal strength to $PCO_2$ or $PO_2$, a requirement for the calculation of CVR. The changes in lung and blood $PCO_2$ during breath-holding are an exponential function with time. Therefore breath holding time is a poor variable to use to quantitate the strength of the stimulus.

B: Inhaling $CO_2$

A second traditional method of changing $PCO_2$ is inspiring gas mixtures containing $CO_2$ via a facemask. This is known to result in a highly variable ventilatory response between subjects leading to a large variability in $P_{ET}CO_2$. Furthermore, inhaling $CO_2$ changes the minute ventilation ($\dot{V}_E$) resulting also in variability in blood $PO_2$. Oxygen is a potent vasoconstrictor and confounds the interpretation of the relationship between $PCO_2$ and brain blood flow.

Therefore, neither breath-holding nor inhaling a gas mixture containing $CO_2$ provide suitable conditions for a consistent, repeatable quantitative test for CVR.

C: Gas Forcing

Since the effects of inhaling a $CO_2$-containing gas mixture on increasing $PCO_2$ can be overcome by increasing minute ventilation, one can introduce a feedback loop to adjust the inhaled $PCO_2$ to effect a target $P_{ET}CO_2$. This is referred to as "gas forcing" (2). Gas forcing has been shown to be effective in imposing target $P_{ET}O_2$ and target $P_{ET}CO_2$ independent of minute ventilation. However, it does have some drawbacks with respect to measuring CVR:

Gas forcing depends on a feedback loop. Feedback loops can have inherent instability depending on the gain and time constant of the system, and are prone to drift and oscillation of end-tidal values.

Gas forcing is usually applied in a chamber or requires a hood over the head. As such, there is a large volume of gas that needs to be replaced rapidly for each change in inspired $PCO_2$. This necessitates very large flows of gases and very precise flow controllers for each gas (such as $N_2$, $O_2$ and $CO_2$ if only these gases are controlled). This is very expensive and cumbersome, and an error which leads to presentation of pure $N_2$ or pure $CO_2$ could be deadly.

Gas forcing requires the construction of a special chamber that is not available commercially and has been custom built for research purposes. This is available only in a few places in the world.

The requirement for specific air-tight chambers, large gas flow controllers, massive volumes of gases, and complex computer control algorithms makes gas forcing too cumbersome to be suitable for use in a radiology, MRI and ophthalmology suites.

The time constant for changes in alveolar gas concentrations is too long to be suitable for use with MRI.

D: Sequential Gas Delivery Method:

A more recent method introduced by Vesely et al. (1) solved some of these problems. They used $O_2$ flow to a sequential gas delivery (SGD) circuit to produce rapid changes in $P_{ET}CO_2$ between two known levels (30-50 mmHg). (A SGD circuit provides (at least) two gases through two breathing circuit limbs. The gas from the first limb ($G^1$) is provided first, and if the subject's breathing exceeds the available first gas, the balance of that breath is made up of the second gas ($G^2$). The second gas may be previously exhaled gas collected in a reservoir on the second limb.) To reduce $PCO_2$, they asked their subjects to hyperventilate while providing large $O_2$ flows into the SGD. To raise the $PCO_2$, they provided a bolus of $CO_2$ by briefly changing the composition of the gas entering the circuit and then maintained the raised $PCO_2$ by controlling the flow into the SGD. While this allowed transitions to a new $P_{ET}CO_2$, the lowering and raising of $O_2$ flows into the circuit to control $P_{ET}CO_2$ and the required changes in $\dot{V}_E$ cause alveolar, and thus end tidal, $O_2$ concentrations to change during the protocol despite near constant inspired $O_2$ concentration. For example, when $O_2$ flow is restricted in order to keep the $P_{ET}CO_2$ high, the $P_{ET}O_2$ tends to drift down (as $O_2$ consumption stays constant in the face of reduced $O_2$ delivery). When subjects hyperventilate to lower the $P_{ET}CO_2$ the increased $O_2$ flow into the circuit results in a rise of $P_{ET}O_2$ (as $O_2$ consumption stays constant and $O_2$ delivery is increased). The changes in blood $PO_2$ have an effect on the MRI signal independent of brain blood flow confounding the interpretation with respect to blood flow.

There are additional practical problems with this method:

Subjects must change their $\dot{V}_E$ frequently during the protocol. It may be difficult for most people to comply adequately with this.

Not adequately following breathing instructions results in not meeting target $PCO_2$ values Not responding to breathing instructions quickly enough invalidate the MRI data.

The method of Vesely et al uses 2 gases and the manipulation of flow into the circuit to change end tidal $CO_2$ values. With this method, if the total flow is set, then varying the inspired $PCO_2$ changes the inspired $PO_2$.

$P_{ET}O_2$ cannot be determined independently of $P_{ET}CO_2$.

$P_{ET}O_2$ and $P_{ET}CO_2$ cannot be varied independently.

Reference List (1) Vesely A, Sasano H, Volgyesi G, Somogyi R, Tesler J, Fedorko L et al. MRI mapping of cerebrovascular reactivity using square wave changes in end-tidal PCO2. Magn Reson Med 2001; 45(6):1011-1013.

(2) Robbins P A, Swanson G D, Howson M G. A prediction-correction scheme for forcing alveolar gases along certain time courses. J Appl Physiol 1982; 52(5):1353-1357.

SUMMARY OF THE INVENTION

In one embodiment, the present invention relates to a method to control the end tidal $CO_2$ and end tidal $O_2$ independently of each other and independently of minute ventilation.

In one aspect, the invention is directed to a method of inducing a target end tidal concentration, or maintaining the end tidal concentration at a target level, of a gas X in a subject comprising:

setting the source gas flow into a partial re-breathing circuit at a rate equal to or less than the subject's minute ventilation;

setting the concentration of said gas X in the source gas to a predetermined level that will induce the end-tidal concentration of said gas X to be at the target end tidal concentration;

delivering the source gas to the subject through said circuit.

Throughout this disclosure, the term subject is intended to be interpreted broadly, and could include, for example, a human adult or child or an animal.

In a second aspect, the invention is directed to a method of inducing target end tidal concentrations, or maintaining end tidal concentrations at a target level, of a plurality of gases in a subject comprising:

setting the source gas flow into a partial re-breathing circuit at a rate equal to or less than the subject's minute ventilation;

setting the concentration in the source gas, of each gas whose target is being induced or maintained, to a predetermined level to attain the target end tidal concentration of that gas;

delivering the source gas to the subject through said circuit.

As further described herein, according to one embodiment of the invention, the concentration in the source gas, of each gas whose end tidal concentration in the subject is being set to or maintained at a target, may be set by using one or more pre-mixed gases as the source gas, the said pre-mixed gas having a minimal safe concentration of oxygen and otherwise concentrations of target gases such as $N_2$ and $CO_2$ so as to provide the required target end tidal concentrations. Alternatively, the concentrations in the source of each gas whose end tidal concentration in the subject is being set to, or maintained at, a target, may be set by blending the source gas from a set of pure component gases, for example $O_2$, $N_2$, and $CO_2$.

Embodiments of the invention may be employed to simultaneously maintain or change the end tidal concentrations of two gases independently of one another. Alternatively, the invention may be employed to maintain the end tidal concentration of a first gas X, while the end tidal concentration of at least one second gas Y is changed from a first target to a second target, by altering the composition of the source gas so that the concentration of the at least one second gas Y is changed.

According to one aspect of the invention the concentration of one or more gases in the source gas flowing into a partial rebreathing circuit may be controlled to achieve a particular target end tidal concentration of those gases when such concentration of such gases in the source are predetermined and set based on one or more steps described herein. As described below, to achieve a target end tidal of a gas X that is physiologically produced by the subject's body, the concentration of said gas X is set using one formula:

$$FG^1X = F_TETX - \frac{\dot{V}X}{\dot{V}G^1}$$

where $F_G^1X$ is the concentration of gas X in the source gas $G^1$, $\dot{V}X$ is the subject's minute production of the physiologically produced gas X, $F_{T}ETX$ is the target end tidal concentration of said gas X, and $\dot{V}G^1$ is the flow rate of the source gas. An example of one such gas would be $CO_2$.

The concentration in the source gas of gases that are physiologically consumed by the subject are set using the formula:

$$FG^1X = F_TETX + \frac{\dot{V}X}{\dot{V}G^1}$$

where $F_G^1X$ is the concentration of gas X in the source gas $G^1$, $\dot{V}X$ is the subject's minute consumption of gas X, $F_{T}ETX$ is the target end tidal concentration of gas X and $\dot{V}G^1$ is the flow rate of the source gas.

The above formulas are applicable in particular when the subject breathes into a partial rebreathing circuit and in particular a circuit such as that shown in FIG. 1a, but is also applicable in any situation where the subject is breathing into a circuit with a flow of gas G1 and a flow of neutral gas G2 which is neutral with respect to the subject's end-tidal concentration of gas X.

The subject's minute production of a physiologically produced gas or minute consumption of a physiologically consumed gas may be estimated based on height and weight, or other parameters, or measured directly.

Whether the source gas can be, at any given time, made up of pre-mixed 'component' gases delivered individually or a blend of constituent gases, is a function of the capability of the apparatus (the apparatus may be adapted to accommodate one or both capabilities depending on its intended use) but is otherwise immaterial to the practice of the invention. In either case according to one preferred embodiment of the invention, the source gas flow into the breathing circuit preferably has a minimum safe concentration of $O_2$, for example 10%. Where the source gas is made up of blended component gases (examples of sets of components gases for providing a full array of target end tidale concentrations are described below), at least the most frequently used and preferably each of the component gases comprises a minimum safe concentration of $O_2$.

In a broader aspect, to achieve one or more changes in the end tidal concentration of a given gas, the invention is directed to a method of changing an end tidal concentration of a gas X in a subject, comprising setting the source gas flow into a partial rebreathing circuit at a rate equal to or less than the subject's minute ventilation and providing a first concentration of said gas X in the source gas and delivering the source gas to the subject through said circuit in order to effect a first end tidal concentration of said gas X.

In a preferred embodiment of the latter method, the further step of providing at least one second different concentration of said gas X in the source gas and delivering the source gas to the subject through said circuit in order to effect a second end tidal concentration of said gas X conveniently enables a diagnostic assessment to be made by measuring a physiological parameter at two end tidal levels of said gas X.

In other aspects, the invention is directed to data acquisition and diagnostic methods employing any of the aforementioned methods of the invention and the various embodiments of those methods described herein and to apparatus adapted to carry out the method and components thereof, optionally including component gases, assembled to carry out the method.

Preferred embodiments of such data acquisition and diagnostic methods include:

A method to measure cerebrovascular reactivity comprising controlling the end tidal $CO_2$ and $O_2$ levels of a subject using one of the aforementioned methods and monitoring cerebral blood flow or oxygenation via some method such as a blood oxygen level dependent (BOLD) or ASL (arterial spin labeling) with functional Magnetic Resonance Imaging signal intensity, trans-cranial Doppler, carotid artery Doppler, Positron Emission imaging, Near Infra-red Spectroscopy.

A method to measure occulovascular reactivity comprising controlling the end tidal $CO_2$ and $O_2$ levels of a subject using one of the aforementioned methods and monitoring occulovascular blood flow.

A method to measure a beneficial level of oxygenation to tissues for the purpose of radiotherapy or chemotherapy, comprising controlling the end tidal $CO_2$ and $O_2$ levels of a subject using one of the aforementioned methods and monitoring oxygenation or blood flow in the skin, muscle, tumor or other tissue.

It will be appreciated that in the practice of the aforementioned diagnostic methods the end tidal $CO_2$ and $O_2$ levels are controlled independently of each other. For example, the end tidal $CO_2$ levels may be changed while the end tidal $O_2$ levels are kept constant or the end tidal $O_2$ levels may be changed while the end tidal $CO_2$ levels are kept constant or the end tidal $O_2$ levels and the end tidal $CO_2$ levels may be changed simultaneously.

In yet another aspect, the invention is directed to a therapeutic method comprising any of the aforementioned methods for controlling end tidal gas concentrations, for example a therapeutic method comprising using such a method to set the end tidal $O_2$ and $CO_2$ levels to pre-determined levels that provide a beneficial oxygenation level or blood flow level to tissues for the purpose of accelerating healing, or increasing sensitivity to ablation by radiotherapy or chemotherapy.

In the practice of one embodiment of one of the aforementioned methods, the partial re-breathing circuit is a sequential gas delivery circuit and the apparatus includes means for controlling the rate of flow of the source gas into the circuit and means for controlling the concentration of said gases in the source gas flow. Optionally, the apparatus further comprises means for monitoring pressure in the breathing circuit and optionally further comprises means for measuring the subject's end tidal gas concentrations.

Optionally, the method above may further comprise measuring the end tidal gas concentrations and using feedback control to increase or decrease the concentrations of a particular gas so as to minimize the difference between the current end tidal concentration and the target end tidal concentration, for example so as to effect a more rapid change in target end tidal levels.

Changes in end tidal $CO_2$ and/or $O_2$ can be used to determine vascular reactivity in cerebral, pulmonary, renal, or retinal vessels and other vascular beds as detected by various blood flow or blood flow surrogate sensors. Similarly, changes in end tidal $CO_2$ and/or $O_2$ can be used to determine changes on organ or tissue function by measuring such factors as blood pressure and heart rate variability, skin conductivity, capillary blood flow in the skin, hormone levels, organ temperature, finger or other limb plethysmography, and other measurements known to physiologists and others skilled in the art.

In yet another aspect, the invention is directed to a method of preparing an apparatus for the use of independently controlling the end tidal concentration of each constituent gas in the expired gas of a subject, comprising:

selecting a rate of a source gas flow into a breathing circuit, the rate projected to be not substantially more than the minute ventilation of the subject;

selecting the composition of said source gas by selecting the concentration of a constituent gas X in the source gas based on a selected end tidal concentration of the constituent gas X, whereby said apparatus is adapted to administer a source gas having a first gas composition. In one aspect, step b) includes mathematical computation of the selected concentration of the constituent gas X based on the selected end tidal concentration of the constituent gas X. In another aspect the invention is directed to the apparatus so prepared, such apparatus comprising at least one component gas inlet port, and conveniently 3 or 4 such ports for controlling selected end tidal concentrations with a series of blended gases.

In yet another aspect, the inventions is directed to a system for independently controlling the end tidal concentration of each constituent gas in the expired gas of a subject, the system comprising a source gas outlet, a plurality of component gas inlets, a flow controller for each component gas, an input device for inputting a selected end tidal concentration of a constituent gas X in the source gas and a processor unit programmable to derive the concentration of said constituent gas X in the source gas based on the end tidal concentration of the constituent gas X in the expired gas, said processor unit operatively connected to each flow controller for setting the respective gas flow rate of said flow controller in order to achieve the derived concentration of said constituent gas X in the source gas.

In one embodiment, the selected concentration of the constituent gas X in the source gas is mathematically computed based on the selected end tidal concentration of the constituent gas X in the expired gas. In another embodiment, the source gas is made up of at least three component gases.

In another embodiment, each component gas inlet is fluidly connected to a blended gas source comprising at least 10% $O_2$. In another embodiment, a source gas outlet port is fluidly connected to a sequential gas delivery circuit, for example, a partial rebreathing circuit.

The system could be developed by preparing it for use with premixed gases of a selected composition such that the need for software to determine inlet concentrations of constituent gases and the need to have flow control on component gases is obviated. It is nonetheless considered within the scope of an embodiment of the present invention.

In yet another aspect, the invention is directed to a method of developing a system for independently controlling the end tidal concentration of each constituent gas in the expired gas of a subject, comprising:
a) making available for acquisition an apparatus having at least a source gas outlet, a plurality of component gas inlets, and a flow controller for each component gas; and
b) facilitating implementation of machine readable instructions to drive a processor unit programmable to derive the concentration of said constituent gas X in the source gas based on the end tidal concentration of the constituent gas X in the expired gas, said processor unit adapted to be operatively connected to each flow controller for setting the respective gas flow rate of said flow controller in order to achieve the derived concentration of said constituent gas X in the source gas. The processor unit may be integrate within the housing of a gas blending apparatus or may have a data input interface for driving the flow controllers. Step b) may include carrying out one or more steps selected from:
developing of said machine readable instructions;
out-sourcing development of said machine readable instructions;
making said machine readable instructions available for acquisition;
providing instructions for acquisition of said machine readable instructions;
providing instructions for use of said machine readable instructions;
providing instructions for development of said machine readable instructions;
providing instructions for acquisition of a processor unit programmed with said machine readable instructions; and
providing instructions for working, updating, upgrading, trouble-shooting, substitution, repair or re-acquisition, of said machine readable instructions or such processor unit. The processor unit may be programmed or have "hard-wired" such instructions.

It will be appreciated that a gas blending apparatus can be made available for acquisition through direct sales or leasing or through collaborating with a third party in the design, development, lease, marketing or sale of an apparatus that is driven by a processor programmed by such machine readable instructions.

The invention contemplates that the system and it method for development can be used with particular gas mixtures that are derived, especially by computation, using the formulas presented herein, thereby obviating the need to calculate these on a case by case basis, and thereby simplifying process control for the component gases. This obviates the need to have individual flow controllers and attendant controls. Therefore in one aspect the system comprises a much simplified apparatus by facilitating its use with specialty gases. In this aspect of the invention the gases may be purchased for use with the system and made be provided with the remainder of the system. In either case instructions the developer facilitates use of the system with the availability of instructions for the use of the specialty gases with a simplified system.

Other aspects and features of the present invention will become apparent, to those ordinarily skilled in the art, upon review of the following description of the specific embodiments of the invention.

BRIEF DESCRIPTION OF THE DRAWINGS

For a better understanding of the present invention, and to show more clearly how it may be carried into effect, reference will now be made, by way of example, to the accompanying drawings, which illustrate aspects of embodiments of the present invention and in which.

DETAILED DESCRIPTION OF THE INVENTION

It should be noted that gas concentrations described herein may be referred to as partial pressures (e.g. $PCO_2$) or as fractional concentrations (e.g. $FCO_2$). Those skilled in the art will recognize the relationship between the two in that partial pressure=fractional concentration x ambient atmospheric pressure.

Glossary Terms

| | |
|---|---|
| Oxygen | $O_2$ |
| Carbon dioxide | $CO_2$ |
| Nitrogen | $N_2$ |
| Partial pressure of oxygen | $PO_2$ |
| Partial pressure of carbon dioxide | $PCO_2$ |

-continued

| | |
|---|---|
| Partial pressure of nitrogen | $PN_2$ |
| Partial pressure of oxygen in end tidal gas | $PETO_2$ |
| Partial pressure of carbon dioxide in end tidal gas | $PETCO_2$ |
| $O_2$ consumption | $\dot{V}O_2$ |
| $CO_2$ production | $\dot{V}CO_2$ |
| Alveolar ventilation | $\dot{V}_A$ |
| Minute ventilation | $\dot{V}_E$ |
| Respiratory quotient | RQ |
| Target end tidal $CO_2$ | $F_T ETCO_2$ |
| Target end tidal $O_2$ | $F_T ETO_2$ |
| Minute ventilation | $\dot{V}_E$ |
| Sequential gas delivery (breathing circuit) | SGD |
| Source gas, or gas inhaled first from an SGD | $G^1$ |
| Reserve gas, or gas inhaled second from an SGD | $G^2$ |
| Flow of fresh gas | $\dot{V}G^1$ |
| Flow of reserve gas | $\dot{V}G^2$ |
| Flow of Gas A | $\dot{Q}_A$ |
| Flow of Gas B | $\dot{Q}_B$ |
| Flow of Gas C | $\dot{Q}_C$ |
| Target end tidal fractional concentration of $CO_2$ | $F_T ETCO_2$ |
| Target end tidal fractional concentration of $O_2$ | $F_T ETO_2$ |
| Fractional concentration of $O_2$ in neutral component of $G^1$ | $FG_n^1 O_2$ |
| Fractional concentration of $CO_2$ in neutral component of $G^1$ | $FG_n^1 CO_2$ |
| Fractional concentration of $CO_2$ in $G^1$ | $FG^1 CO_2$ |
| Fractional concentration of $O_2$ in $G^1$ | $FG^1 O_2$ |

In the present invention the subject preferably breathes through a breathing valve manifold with breathing tubes (herein referred to as a breathing circuit) known as a partial rebreathing circuit. Preferably, the subject breathes on a partial rebreathing circuit that is also a sequential gas delivery (SGD) circuit, whose functions will be reviewed briefly.

Figure 1:
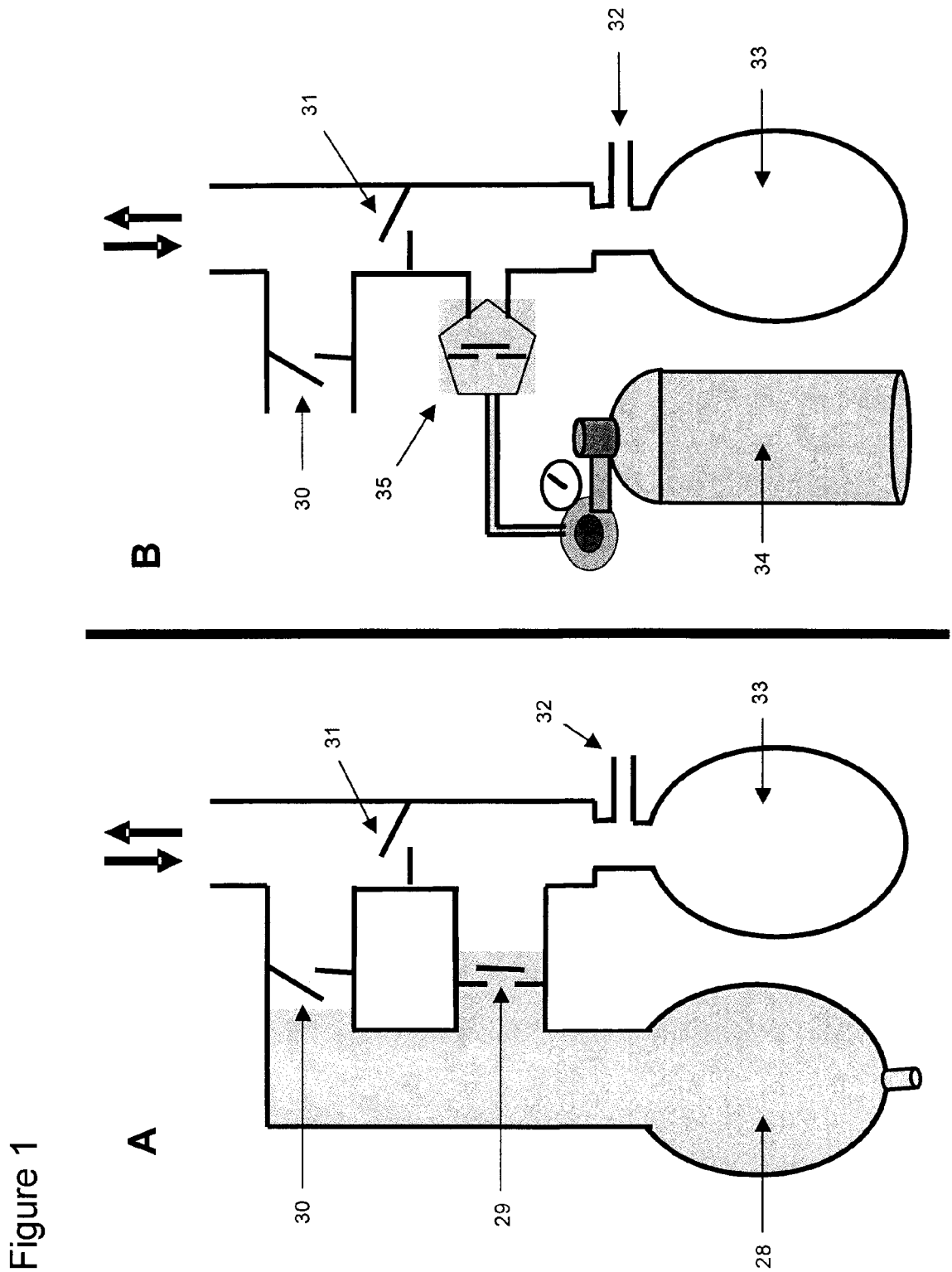
FIG. 1A shows a rebreathing sequential gas delivery circuit.
FIG. 1B shows a non-rebreathing sequential gas delivery circuit.

The non-rebreathing sequential gas delivery circuit was taught by Fisher [U.S. Pat. No. 6,354,292]. The rebreathing sequential gas delivery circuits were taught by Fisher [U.S. Pat. Nos. 6,622,725, 6,612,308]. FIG. 1B illustrates the principles of a non-rebreathing sequential gas delivery circuit. During exhalation, the expiratory one-way valve (30) opens and gas is exhaled to atmosphere; meanwhile, the source gas enters the source gas port (32) and is stored in the source gas reservoir (33). FIG. 1A illustrates the homologous circuit where exhaled gas is used as reserve gas. With this circuit, during exhalation, exhaled gas is directed into an exhaled gas reservoir (28) and made available to act as reserve gas. During inhalation, the one-way inspiratory valve (31) opens and source gas from the source gas port (32) and the source gas reservoir (33) are inhaled. In both of these circuits, when $\dot{V}_E$ exceeds source gas flow, the difference between $\dot{V}_E$ and source gas flow is made up of reserve gas which is presented through crossover valve (29) in the rebreathing circuit or via demand valve (35) in the non rebreathing circuit. Source gas and reserve gas are inhaled sequentially: at the beginning of inhalation, gas is inhaled from the fresh gas flow inlet and the fresh gas reservoir. Reserve gas in the non rebreathing circuit is comprised of gas that has similar properties to exhaled gas.

Description of Method to Independently Control End-Tidal Gases

The present invention describes a method for independent control of end tidal (end of exhalation) gas concentrations of a subject. The discussion herein describes the method particularly as it pertains to control of $CO_2$ and $O_2$, although those skilled in the art will recognize that the method can be equally applied to control of other gases in the subject.

The method comprises:
 determining or estimating the subject's $\dot{V}CO_2$ and $\dot{V}O_2$
 setting the initial flow rate of the source gas ($\dot{V}G^1$) into a partial rebreathing circuit, preferably a sequential gas delivery circuit, on which the subject is breathing, approximately equal to the subject's average $\dot{V}_A$ (discussed further below). This may be accomplished by adjusting the source gas flow until the source gas reservoir of a sequential gas delivery circuit just empties on each breath, or alternatively, a flowmeter may be interposed between the subject and the circuit.

setting the $O_2$ and $CO_2$ concentrations in the source gas ($FG^1 O_2$ and $FG^1 CO_2$ respectively) to concentrations determined using the methods described below A partial rebreathing circuit is required with the method since the end tidal concentrations when breathing on such a circuit become fixed (approximately fixed for most partial rebreathing circuits, and reliably fixed with sequential gas delivery circuits) and independent of minute ventilation ($\dot{V}_E$), provided the gas flow into the circuit is less than or equal to the $\dot{V}_E$. The end tidal concentrations become a function only of the gas concentrations of the source gas.

We will first describe the method for determining $FG^1 CO_2$. In order to carry out the method, one must first obtain values for the subject's $CO_2$ production ($\dot{V}CO_2$), which can be done by direct measurement (for example by analyzing a timed collection of exhaled gas for $FCO_2$) or calculated from standard tables based on other anthropomorphic data such as weight and height.

The method makes use of the relationship known in the art that relates a rate of alveolar ventilation $\dot{V}_A$ to the subject's fractional end tidal $CO_2$ concentration:

$$F_{ET}CO_2 = \frac{\dot{V}CO_2}{\dot{V}_A} \qquad \text{Equation (4)}$$

This relationship states that for a given rate of alveolar ventilation, a particular end tidal concentration is produced. Lowering the alveolar ventilation raises $F_{ET}CO_2$ and raising it lowers $F_{ET}CO_2$.

As long as the subject's minute ventilation exceeds the $\dot{V}G^1$ the composition of $G^1$ determines the end-tidal concentrations of a gas. For example, consider a case where the subject has a resting $\dot{V}_A$ with a corresponding resting end tidal $PCO_2$. We may wish to increase the source gas flow $\dot{V}G^1$ to greater than the subject's resting $\dot{V}A$ to effect a more rapid transition in end-tidal $PCO_2$ or $PO_2$. We instruct the subject to breathe at a rate $\geq \dot{V}G^1$ to assure that all of $\dot{V}G^1$ reaches the alveoli, then additional $CO_2$ in $G^1$ prevents a reduction in $P_{ET}CO_2$. To calculate the concentrations of constituent gases to $G^1$ is to mathematically split $G^1$ into a portion with a flow rate equal to the resting $\dot{V}_A$ and a portion with the balance of the flow which is ($G^1 - \dot{V}_A$). We call the portion that is equal to $\dot{V}_A$ "fresh" gas flow because it contributes to gas exchange, ($\dot{V}G^1_f$) by virtue of having no $CO_2$. This gas flow therefore determines the end tidal concentration according to Equation (4). The second portion of $G^1$ consisting of the difference between the desired $G^1$ and the $\dot{V}_A$ ($G^1 - \dot{V}_A$) requires a concentration of $CO_2$ that does not provide a gradient for gas exchange. Thus composed, it is considered a "neutral" gas flow ($\dot{V}G^1_n$). $FG^1_n CO_2$ equal to that of alveolar gas (as approximated by end tidal gas) by definition would be "neutral" with respect to gas exchange of $CO_2$.

Since there is no $CO_2$ in $\dot{V}G^1_f$, $\dot{V}G^1_n$ is the source of all of the $CO_2$ in $G^1$ (Equation (6)).

$$\dot{V}G^1 \times FG^1 CO_2 = \dot{V}G^1_n \times FG^1_n CO_2 \qquad \text{Equation (6)}$$

In that case, the concentration in the neutral gas must be equal to the target $CO_2$ concentration to maintain $P_{ET}CO_2$ at the target value $$\dot{V}G^1 \times FG^1 CO_2 = \dot{V}G^1_n \times F_T ETCO_2 \qquad \text{Equation (7)}$$

and the rate of flow of neutral gas is the difference between the rate of flow of the source gas and the rate of the subject's alveolar ventilation, or $$\dot{V}G^1_n = [\dot{V}G^1 - \dot{V}_A]$$ Equation (7b)

This allows us to rewrite Equation (7) as:

$$\dot{V}G^1 \times F_G{}^1CO_2 = [\dot{V}G^1 - \dot{V}_A] \times F_TETCO_2$$ Equation (7c)

Also, the relationship between the subject's target end tidal and alveolar ventilation is known from Equation (4).

$$\dot{V}_A = \frac{\dot{V}CO_2}{F_TETCO_2}$$ Equation (4)

Therefore, substituting Equation (4) in equation (7c) we get:

$$\dot{V}G^1 \times FG^1CO_2 = \left[\dot{V}G^1 - \frac{\dot{V}CO_2}{F_TETCO_2}\right] \times F_TETCO_2$$ Equation (8)

Dividing both sides by $\dot{V}G^1$ gives:

$$FG^1CO_2 = F_TETCO_2 - \frac{\dot{V}CO_2}{\dot{V}G^1}$$ Equation (9)

This argument should hold generically for any gas that is absorbed by the body as well. In practice, it is preferable to have the subject breathing at a rate greater than their resting breathing rate in order to achieve end tidal $CO_2$ targets below their resting levels. Additionally, having the subject breathe faster enables more rapid transitions between end tidal levels, particularly when moving from higher to lower $CO_2$ targets, since the breathing rate becomes the limiting factor when giving the lowest concentration (i.e. 0%) of $CO_2$ possible.

We now describe the method for determining $F_G{}^1O_2$. In order to carry out the method, we obtain values for the subject's $O_2$ consumption ($\dot{V}O_2$), which can be done by direct measurement (for example by collecting exhaled gas in a bag and analyzing its concentration), calculated from standard tables based on other physiological data such as weight and height, or determined from $\dot{V}CO_2$ and the Respiratory Quotient (RQ) which relates $\dot{V}O_2$ to $\dot{V}CO_2$ and is usually estimated as having a value of 0.8 in most people.

$$\dot{V}O_2 = \frac{\dot{V}CO_2}{RQ}$$ Equation (5)

The method for determining $F_G{}^1O_2$ is analogous to determining $F_G{}^1CO_2$ with the exception that the sign on the $\dot{V}O_2$ is reversed in Equation (9) reflecting the fact that $O_2$ is consumed by the body while $CO_2$ is produced by the body. Thus the analogous form for Equation (9) as is pertains to $O_2$ is as follows:

$$FG^1O_2 = F_TETO_2 + \frac{\dot{V}O_2}{\dot{V}G^1}$$ Equation (11)

It will be appreciated by those skilled in the art that Equations 9 and 11 may respectively be generalized to any gas that is physiologically produced (as is $CO_2$) or consumed (as is $O_2$) by the body. The general form of Equation 9 for inducing or maintaining a target end tidal concentration of a gas X that is physiologically produced by the body would thus be to set the concentration of gas X in the source gas (defined as $F_G{}^1X$) using $$FG^1X = F_TETX - \frac{\dot{V}X}{\dot{V}G^1}$$ Equation (12)

where $\dot{V}X$ is the subject's minute production of gas X, $F_TETX$ is the target end tidal concentration of gas X, and $\dot{V}G^1$ is the flow rate of the source gas.

The general form of Equation 11 for inducing or maintaining a target end tidal concentration of a gas X that is physiologically consumed by the body would thus be to set the concentration of gas X in the source gas (defined as $F_G{}^1X$) using $$FG^1X = F_TETX + \frac{\dot{V}X}{\dot{V}G^1}$$ Equation (13)

where $\dot{V}X$ is the subject's minute production of gas X, $F_TETX$ is the target end tidal concentration of gas X, and $\dot{V}G^1$ is the flow rate of the source gas.

Optionally, it will be appreciated by those skilled in the art that the method above may be used to target particular end tidal concentrations, however, the targeting may be fine tuned, or the target may be reached more quickly, by measuring the end tidal gas concentrations and using feedback control to increase or decrease the concentrations of a particular gas so as to minimize the difference between the current end tidal concentration and the target end tidal concentration.

Selection of Source Gases

Another aspect of the present invention is the selection of gases used to carry out the method. It will be appreciated by those skilled in the art that, for a given desired total flow, any combination of concentrations of $CO_2$ and $O_2$ in the source gas may be achieved by mixing source gases consisting of pure $O_2$, $CO_2$ and $N_2$. However, pure $CO_2$ and pure $N_2$ contain no $O_2$ and thus if the gas blending apparatus were to fail and the subject were to inhale just a few breaths of either of these two gases, it would lead to severe hypoxemia and possibly death. One aspect of the present invention is the use of source gases each of which has at least a minimum concentration of $O_2$ determined to be the safe minimum level. Preferably, this level is at least 10%, but under certain controlled and monitored conditions, levels less than 10% might still be used.

The gas concentrations are chosen subject to the following constraints:

To achieve a high signal / noise ratio for diagnostics, a wide range of $F_{ET}O_2$ and $F_{ET}CO_2$ values is desirable.

Each gas may have a minimum safe concentration of oxygen, such that if it is the only gas given, the subject will not be severely harmed. This is preferably about 10%. One gas (call it gas "C") may have no more $O_2$ than this and a low level of $CO_2$ to achieve the combination of low target $F_TETO_2$ and low $F_TETCO_2$.

The minimum oxygen concentration of one gas (call it gas "A") may be set so as to achieve the maximum $F_{ET}O_2$ desirable to give the subject.

One gas (call it Gas "B") may also contain at least a high enough $CO_2$ concentration so as to be able to achieve the maximum $F_{ET}CO_2$ desired. The concentration of $CO_2$ in Gas B is further constrained by the fact that, to get a high $F_{ET}O_2$ and high $F_{ET}CO_2$ simultaneously, a substantial amount of Gas A (high $O_2$ concentration) would be given, leaving less room for Gas B in the $\dot{V}G^1$. For example, to achieve a 7.5% $F_{ET}CO_2$ with a 90% $F_{ET}O_2$, Gas A would have over a 90% concentration of $O_2$ and Gas B would have at least a 60% concentration of $CO_2$.

The $O_2$ concentration of Gas "B" may be low enough to enable producing in the subject the highest desirable $F_{ET}CO_2$ and the lowest desirable $F_{ET}O_2$.

Gas "A" may have a low $CO_2$ concentration since it contains a high $O_2$ concentration, and it may be desirable to have a high $F_{ET}O_2$ and low $F_{ET}CO_2$, which cannot be achieved any other way once the constraints on gases B and C above are considered.

Therefore, based on the above constraints, the preferred method includes using gases with relative concentrations as described in Table 1:

TABLE 1

Relative concentrations of $O_2$ and $CO_2$ in Gas A, Gas B and Gas C

| | $FO_2$ | $FCO_2$ |
|---|---|---|
| Gas A | High (for greater range of maximum target end tidal $O_2$ - preferably 100%) | Low (maximum lower bound range for end tidal $CO_2$ - preferably 0%) |
| Gas B | The Safe Minimum $O_2$ concentration - preferably 10% | High (for greater range of maximum target end tidal $CO_2$ - preferably 20%-80%) |
| Gas C | The Safe Minimum $O_2$ concentration - preferably 10% | Low (maximum lower bound range for end tidal $CO_2$ - preferably 0%) |

Blending Source Gases to Achieve the Required Total Gas Concentrations of $CO_2$ and $O_2$ For the present discussion, we assume that the $FO_2$ in Gas B and Gas C are set to achieve the lower bound of $F_TETO_2$, and $FCO_2$ in Gas A and Gas C are both set to achieve the lower bound $F_TETCO_2$. Hence, the greatest range of $F_TETO_2$ and $F_TETCO_2$ occurs when $FBO_2=FCO_2$ and $FACO_2=FCCO_2$. Table 2 is used to defines terns used to designate the $O_2$ and $CO_2$ concentrations in Gas A, Gas B and Gas C.

TABLE 2

Definition of terms used to designate the $O_2$ and $CO_2$ concentrations in Gas A, Gas B and Gas C.

| | Fractional $O_2$ concentration | Fractional $CO_2$ concentration |
|---|---|---|
| Gas A | $FAO_2$ | $FACO_2$ |
| Gas B | $FBO_2$ | $FBCO_2$ |
| Gas C | $FBO_2$ | $FACO_2$ |

The method summarized by Equations 11 and 9 are used to determine fractional concentrations of $CO_2$ and $O_2$ that have to be supplied in $G^1$ to attain target $F_TETCO_2$ and $F_TETO_2$, assuming the subject's or subject's $\dot{V}CO_2$ and $\dot{V}O_2$ are known.

The total flow of source gas $G^1$ into the apparatus is the sum of the flows of the individual gases A, B and C.

$$\dot{V}G^1 = \dot{Q}_A + \dot{Q}_B 30 \, \dot{Q}_C$$

The flow of $O_2$ in the source gas is equal to the sum of the flows of $O_2$ from the individual gases. Therefore:

$$\dot{V}G^1 \times F_G{}^1 O_2 = \dot{Q}_A \times F_A O_2 + \dot{Q}_B \times F_B O_2 + \dot{Q}_C \times F_C O_2$$

But since $FCO_2=FBO_2$ this can be rewritten as $$\dot{V}G^1 \times F_G{}^1 O_2 = \dot{Q}_A \times F_A O_2 + (\dot{V}G^1 - \dot{Q}_A) \times F_B O_2$$

which simplifies to $$\dot{Q}_A = \frac{\dot{V}G^1(FG^1O_2 - FBO_2)}{FAO_2 - FBO_2} \qquad \text{Equation (1)}$$

The flow of $CO_2$ in the source gas is equal to the sum of the flows in the individual gases. Therefore:

$$\dot{V}G^1 \times F_G{}^1 CO_2 = \dot{Q}_A \times F_A CO_2 + \dot{Q}_B \times F_B CO_2 + \dot{Q}_C \times F_C CO_2$$

But since $FACO_2=FCCO_2$ this can be rewritten as $$\dot{V}G^1 \times F_G{}^1 CO_2 = \dot{Q}_B \times F_B CO_2 + (\dot{V}G^1 - \dot{Q}_B) \times F_A CO_2$$

This simplifies to $$\dot{Q}_B = \frac{\dot{V}G^1(FG^1CO_2 - FACO_2)}{FBCO_2 - FACO_2} \qquad \text{Equation (2)}$$

Finally, $$\dot{Q}_C = \dot{V}G^1 - \dot{Q}_A - \dot{Q}_B \qquad \text{Equation (3)}$$

Equations 1, 2 and 3 can be used to calculate flows required from each mixture to obtain a total flow ($\dot{V}G^1$) with $O_2$ concentration of $FG^1O_2$ and $CO_2$ concentration $FG^1CO_2$. It should be appreciated by those skilled in the art that other gas combinations for component gases may be used, and the derivation above may be extended to the general case of any concentration for any gas in the component gas. The same method and approach that is described for $O_2$ can be applied to any other gas that is absorbed, including, but not limited to acetylene, carbon monoxide, nitrous oxide, anesthetic gases. It is recognized that by defining target $PCO_2$ and target $PO_2$, target $PN_2$ is also defined. In the same way, the target partial pressure of any inert gas can be defined, for example, but not limited to argon, helium, and xenon.

Another aspect of this invention is the use of the independent control of end tidal $CO_2$ and $O_2$, $N_2$ or other gas levels to carry out diagnostic and therapeutic tests or carry out research in physiology. What follows are examples that are not meant to be an exhaustive list of applications for instituting targeted blood gases. For example, the $CO_2$ levels may be rapidly transitioned from low to high targets and back repeatedly while the subject's brain blood flow is measured using the Blood Oxygen Level Dependent (BOLD) MRI imaging technique. This produces a map of cerebrovascular reactivity. BOLD and transcranial Doppler, for example can be used to measure the physiology of brain and other tissue blood flow response to changes in blood concentrations of $CO_2$, $O_2$, with or without the presence of other gases or substances in the blood. Similarly, occulovascular reactivity may be measured by measuring blood flow in the retinal vessels with Doppler ultrasound, MRI or other devices known to those skilled in the art, at target concentrations of $CO_2$, $O_2$ and other gases, with and without the presence of other substances in the blood. Another test involves manipulating $O_2$ levels in tumors and measuring beneficial oxygenation levels in the tumor using BOLD MRI signal or other methods known to those skilled in the art. This would identify blood gasses providing beneficial levels of blood flow and oxygenation to tumors, sensitizing them to destruction by radiotherapy or chemotherapy. This may additionally be combined with using the method during radiotherapy so as to reproduce the determined level of oxygenation. It is obvious that similar studies may be performed in any of the other responsive vascular beds in the body including but not limited to the skin, kidney, heart, lung and various abnormal congenital and acquired conditions such as tumours and vascular malformations.

Being able to achieve target end tidal $PO_2$ and $PCO_2$ allows the reproducibility of test conditions. This in turn allows the comparison of tests on one subject from one time to the next and between subjects. This reproducibility of the test enables the doctor, for the first time, to follow the progress of an abnormality, or a response to treatment. For example, in a subject with Moyamoya disease, an area of the brain develops abnormalities in blood vessels which can be identified by abnormal response to changes in $PCO_2$. Repeated standardized tests to the same target $PCO_2$ allows the doctor to identify changes in strength of response. In cranial artery stenosis, an area of the brain may lose its vascular reactivity as seen by response to BOLD imaging with MRI in response to changes in $PCO_2$. The test can be repeated after surgery to identify the extent of recovery of vascular reactivity. If there are still areas of loss of reactivity, further surgery may be indicated.

A standardized test allows the study of the normal physiology of control of blood flow to a tissue or organ that responds to $CO_2$ or $O_2$. For example, trans cranial Doppler, BOLD MRI, spin labeling with MRI, Positron Emission Tomography or many other measurements known to those skilled in the art can be used to measure blood flow, oxygenation or metabolism of tissues and organs in response to known, reproducible changes in $PO_2$ and $PCO_2$ or other gases with this method.

In summary, this invention provides the ability to provide standard, reproducible stimuli via the lung to vascular beds and other tissues. When combined with any of a long list of sensors, known to those skilled in the art, a standard set of stimuli allows the comparison of results in a subject over time, between subjects in a group, of a group over time, and between groups being studied by different researchers. None of these advantages can be obtained from known methods that do not reliably provide reproducible stimuli.

Alternate Method Using Premixed Gases

Equations 9 and 11 above disclose the method for determining the fractional concentrations of $CO_2$ and $O_2$ in the source gas based on the target end tidal concentrations and the subject's rate of $O_2$ consumption and $CO_2$ production. It may be desirable for performance of certain diagnostic tests to assume that a particular subject population has a small range of values for $CO_2$ production and $O_2$ consumption, or to ignore the small variations that the differences in these values might make to the resulting end tidal concentrations. It would then be possible to use a plurality of gas mixtures with predetermined concentrations of gas to achieve particular sets of targets. For example, assuming all subjects had a $\dot{V}O_2$ of 300 ml/min, $\dot{V}CO_2$ of 250 ml/min, and breathed at a rate of $\dot{V}_E$=10 lpm, and given the following set of target end tidal concentrations of $CO_2$ $O_2$, one might provide the following premixed gases each of which corresponded to one pair of targets. These gases may be provided to the subject in a predetermined sequence to perform a diagnostic test, for example.

TABLE

Sample Premixed Gases to Achieve Desired set of Targets

| Gas | $F_TETO_2$ | $F_TETCO_2$ |
|---|---|---|
| D (1.5% $CO_2$, 52.5% $O_2$, Bal. $N_2$) | 50% | 4.0% |
| E (3.7% $CO_2$, 22.5% $O_2$, Bal. $N_2$) | 20% | 6.2% |
| F (2.6% $CO_2$, 72.5% $O_2$, Bal. $N_2$) | 70% | 5.1% |

End Tidal Control Apparatus

Figure 2:
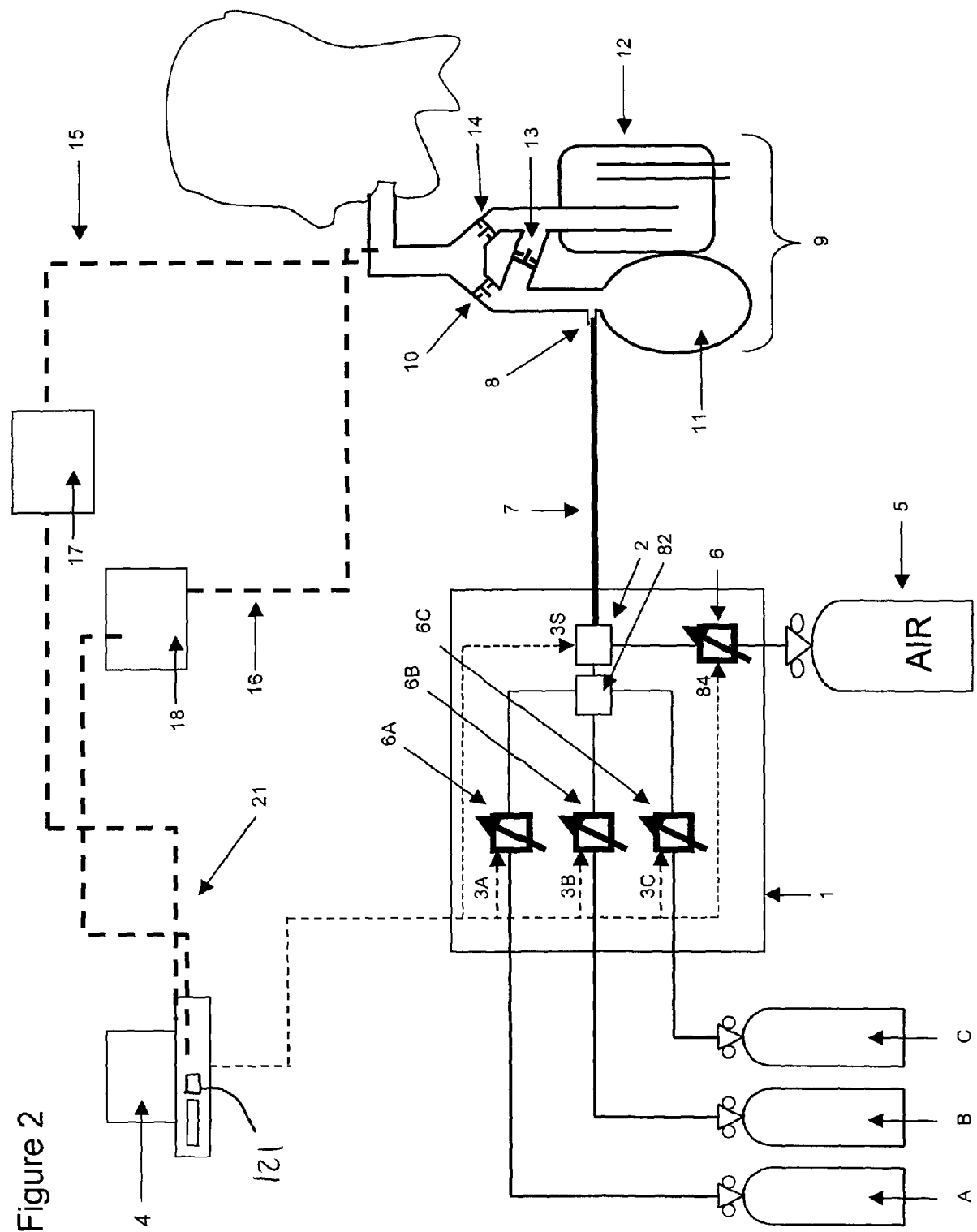
FIG. 2 shows the preferred embodiment of the apparatus.

Another aspect of the present invention is the apparatus used to carry out the method. The apparatus may include source gases chosen to provide the maximum range of combinations of targets for the end tidal gases, a gas blending device and a partial rebreathing circuit. In the preferred embodiment, the gases to be controlled are $O_2$ and $CO_2$. With reference to FIG. 2, three pressurized gases A, B and C (which may be referred to as component gases A, B, and C) are connected to the gas blending apparatus (1). When the method is conducted, gases A, B and C are delivered to the blender (1) at flows $\dot{Q}_A$, $\dot{Q}_B$ and $\dot{Q}_C$ that are regulated by flow controllers (6A), (6B) and (6C) via control inputs (3A), (3B) and (3C) respectively. These flow controllers (6a), (6B) and (6C) may be of many types known in the art, but are preferably mass flow controllers to enhance precision. The control inputs (3A), (3B) and (3C) may be provided via an operative connection between a processing unit (4) and the flow controllers (6A), (6B) and (6C). The processing unit (4) may derive the appropriate control inputs (3A), (3B) and (3C) by looking up values from a database based on the target end tidal values for whatever gas or gases is/are selected to be controlled. The database values would be based on the formulas 9 and 11 discussed above. The processing unit (4) could alternatively calculate the data for the control inputs (3A), (3B) and (3C) directly based on the formulas 9 and 11 discussed above. The processing unit (4) may be any suitable type of processing unit, such as a computer, and may optionally include a screen and/or other output device. The processing unit (4) may be integral with other components, such as the gas blender (1), such that they are held in a common housing. Alternatively, the processing unit (4) may be a separate item that may or may not be supplied with the rest of the system. For example, the processing unit (4) may be supplied by the customer.

Appropriate software 121 for use in controlling the flow controllers 6A, 6B and 6C as described above may be provided with the system. In embodiments wherein the processing unit (4) is provided as part of the system, the software 121 may be provided pre-installed on the processing unit (4). In embodiments wherein the processing unit (4) is expected to be supplied by the customer, the software may accompany the system so that the customer can install the software on their own processing unit (4). Alternatively the software may be provided in some other way. For example, the software may be downloadable remotely by the customer, for example, over the internet. In a situation where the software is supplied over the internet by means of permitting the customer to download the software, it is nonetheless to be considered as having been supplied as part of the system, whether or not the processing unit 4 is also included or is expected to be supplied by the customer.

For clarity, the concept of controlling the flows of the component gases A, B and C comprises setting the flows of the gases A, B and C to achieve selectable concentrations for at least two of the constituent gases that are contained in the combined flow of the gases A, B and C. It is alternatively possible to provide an apparatus with one or more gas inlets, wherein the one or more component gases connected to the one or more gas inlets already have a preselected concentration of gases in them, so that no flow control is needed on any individual component gas. For example, a single component gas could be used, which already contains a selected concentration of the gases to achieve a particular desired end tidal concentrations. This may be applicable in certain diagnostic situations for example, where a subject is brought to a selected set of end tidal conditions that are consistent from subject to subject.

The concept of controlling the end tidal gas concentrations of a plurality of gases comprises selecting the end tidal gas concentrations for a plurality of gases and setting the concentrations of gases in the source gas flow to achieve the selected end tidal conditions. It may be that one of the gases, for example, is selected to be maintained at constant concentration in the end tidal gas.

Flows of $\dot{Q}_A$, $\dot{Q}_B$ and $\dot{Q}_C$ are determined according to the present method for target $F_{ET}CO_2$ and $F_{ET}O_2$ at each phase in the sequence. The blend of $\dot{Q}_A$, $\dot{Q}_B$ and $\dot{Q}_C$ results in $\dot{V}G^1$. The resulting mixture, $G^1$, leaves the blender (1) via an output hose (7) and is delivered to the gas inlet (8) of the partial rebreathing circuit (9). In the preferred embodiment shown, the partial rebreathing circuit is a sequential gas delivery circuit. During inhalation, inspiratory one-way valve (10) opens and the first part of the breath comes from the gas inlet (8) and $G^1$ reservoir (11). If $\dot{V}_E$>exceeds $\dot{V}G^1$, the $G^1$ reservoir (11) collapses during the breath and the balance of the breath comes from the exhaled gas $G^2$ reservoir (12) via the crossover valve (13) or in the case of a non-rebreathing SGD from stored exogenous gas that approximates exhaled gas.

During exhalation, expiratory one-way valve (14) opens and expired gases are either collected in the exhaled gas reservoir (12), or in the case of a non-rebreathing SGD, they are vented. Meanwhile, $G^1$ collects in the $G^1$ source gas reservoir (11). Optional pressure sampling line (15) and pressure transducer (17) can be inserted at the subject-circuit interface to aid in synchronization of changes in gas flows with the breath. Optionally, gas may be sampled via line (16) connected to an optional $CO_2/O_2$ analyzer (18). Peak detection algorithm can use signals from pressure transducer (17) or gas analyzer to detect breaths and pick end-tidal values for $O_2$ and $CO_2$. Data can be analyzed on- or off-line and displayed on a computer screen that is optionally part of the processing unit (4).

Optionally, if it is desired to give the subject air during a stand by phase, three-way solenoid valve (2) is electronically controlled by connection (3S) from machine intelligence (4) and is either open to air source (5) or to the manifold (82) collecting gas from gas sources A, B and C. When the apparatus is in the standby mode, the subject receives air flow which is regulated by flow controller (6) via control input (84).

Alternate Embodiment

Figure 3:
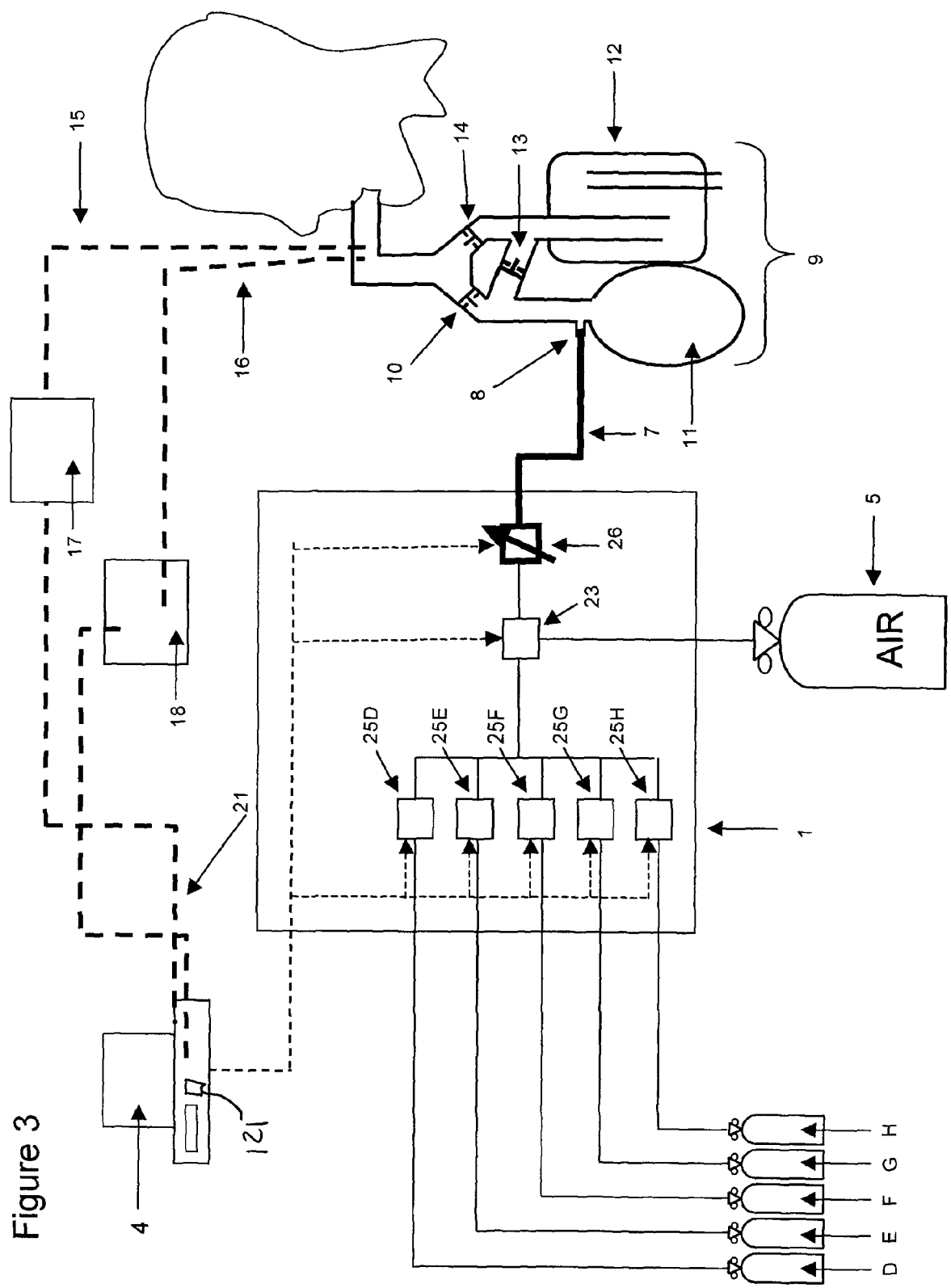
FIG. 3 shows an alternate embodiment of the apparatus.

If it is desired to "hardwire" a particular sequence of target end tidal concentrations, premixed gases with concentrations to achieve the desired targets can be used with an alternative apparatus described in FIG. 3. For any given pattern of transitions and steady states, individual concentrations of $O_2$ and $CO_2$ in the $G^1$ gas measured among different subjects will depend on subject's $\dot{V}O_2$ and $\dot{V}CO_2$. In order to accommodate for these differences, apparatus described in FIG. 3 allows precise control of $\dot{V}G^1$ according to the subject's $\dot{V}O_2$ and $\dot{V}CO_2$ or estimate thereof.

With reference to FIG. 3 a set of premixed gases (5 are shown, but one is needed for each set of target end tidal concentrations) D, E, F, G and H containing premixed mixtures of $O_2$, $CO_2$ and $N_2$ equal to those required in the $G^1$ gas during each phase of the sequence, are connected to gas blender (1). Two-way solenoid valves (25D, 25E, 25F, 25G, 25H) control the flow of gases D, E, F, G and H. The two-way solenoid valves (25) are controlled by machine intelligence (4), which contains pre-programmed information about the order and duration of opening of each individual valve. Gas flow to the circuit (9) is regulated by a flow controller (26). Optional three-way solenoid valve (23) is electronically controlled via machine intelligence (4) and may be open to optional air source (5) during an optional stand by phase or to the gases coming through solenoids (25). The rest of the apparatus may be the same as in FIG. 2.

Figure 4:
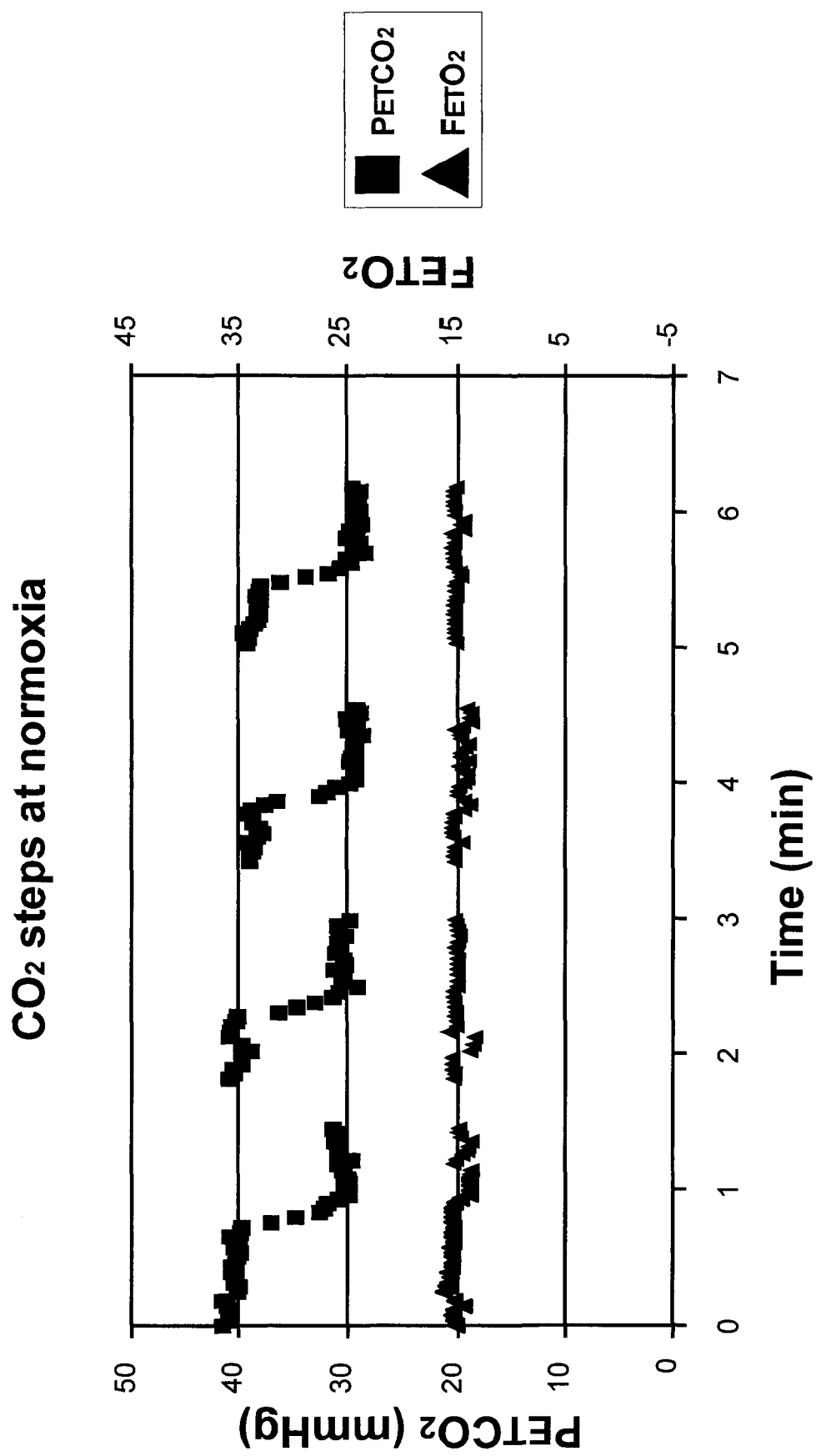
FIG. 4 shows data from a subject using the apparatus and method, with constant $P_{ET}O_2$ and changes in levels of $P_{ET}CO_2$.
Figure 5:
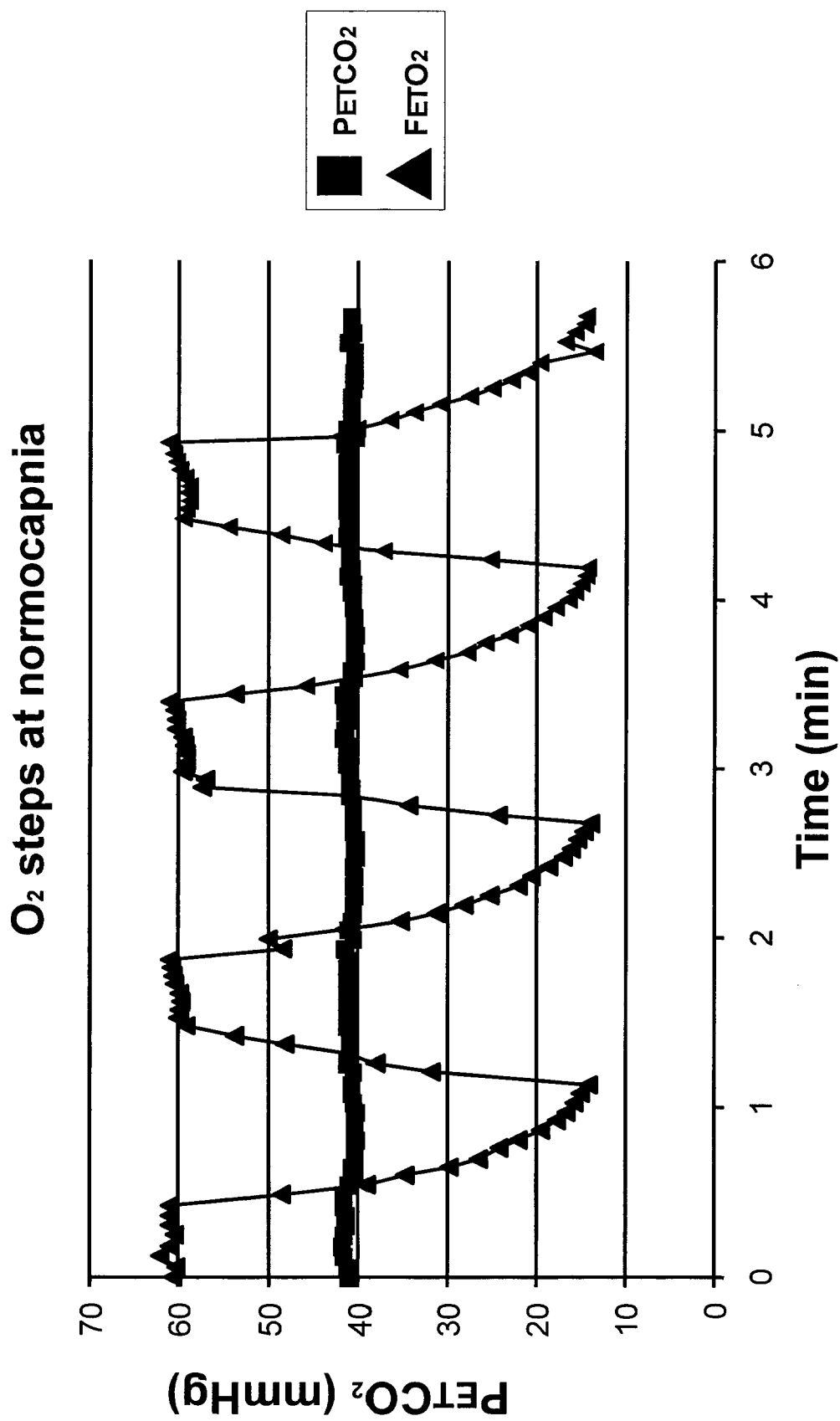
FIG. 5 shows data from a subject using the apparatus and method, with constant $P_{ET}CO_2$ and changes in levels of $P_{ET}O_2$.
Figure 6:
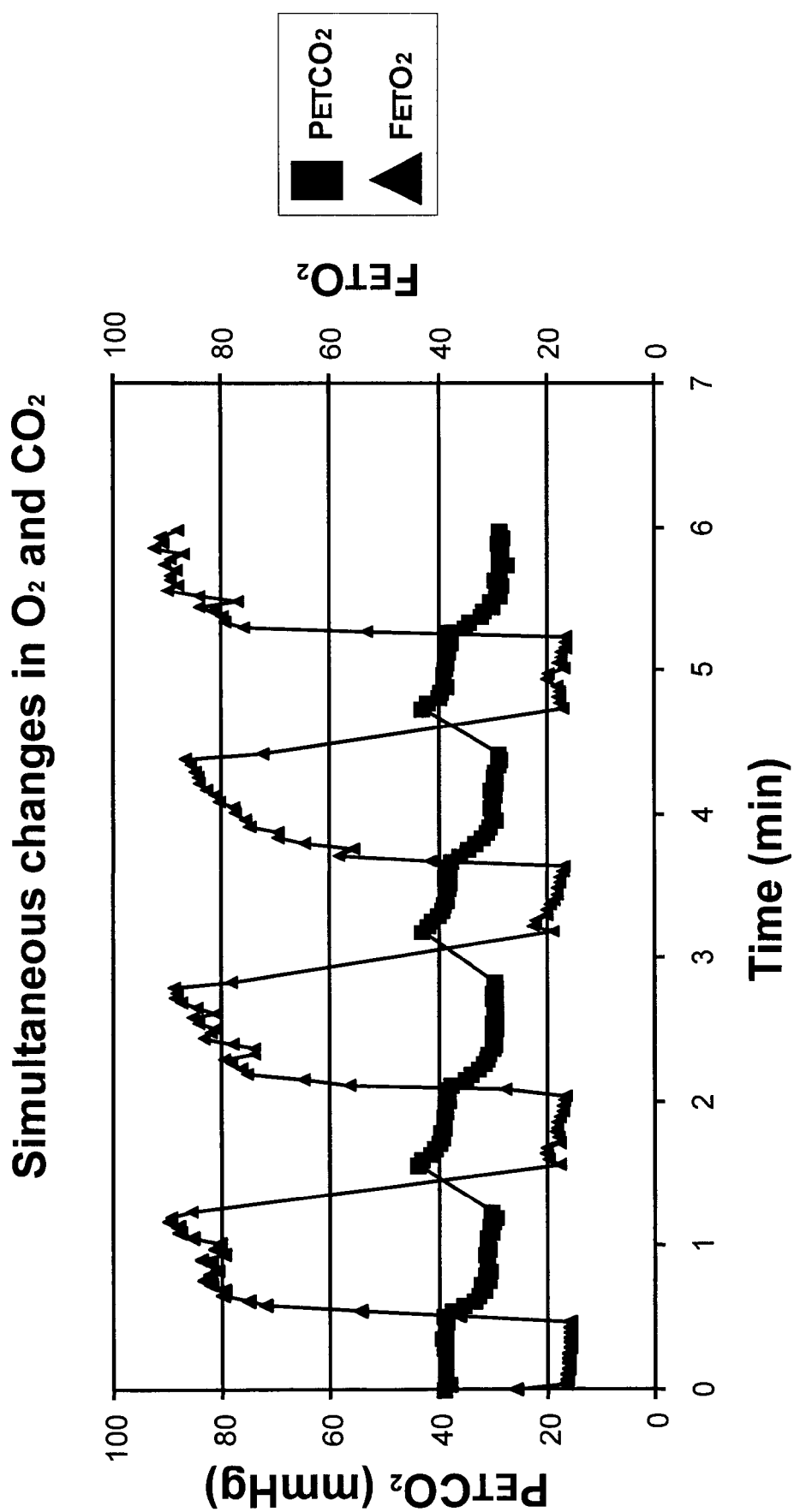
FIG. 6 shows data from a subject using the apparatus and method, with simultaneous controlled changes in $P_{ET}CO_2$ and $P_{ET}O_2$.

FIGS. 4-6 show experimental data obtained from a subject whose end tidal values were controlled and set to target levels.

The term "selecting" in reference to "selecting" the rate of flow of the source gas does not necessarily imply that the apparatus is of a character where the rate must be adjustable. Strictly speaking the implication is that an operator need only prepare for use an apparatus with a rate of flow suitable to the task at hand, particularly where only a single rate of flow is acceptable. Nevertheless, it will be appreciated that an adjustable rate of flow adds considerable flexibility to the way the apparatus can be used. For example, where a rapid change of one or more end tidal target gas concentrations is sought to be effected, setting the flow rate to be faster, with rapid breathing expected of the subject, permits more rapid alveolar gas exchange.

The term "source gas" is understood to mean the gas ultimately flowing to and inhaled by the subject. This gas may be made up of one or more "component gases", namely individual gases comprising one or more "constituent gases". Constituent gases are invariably understood to mean substantially "pure" gases in terms of their molecular make up eg. 100% $O_2$. Where a component gas comprises more than one constituent gas, this component gas is frequently referred to herein as a "mixed" or "blended" gas. However, in a particular context, a reference to a blended or mixed gas could possibly also be understood to refer to the source gas itself.

It will be understood that selecting the concentration of the at least one constituent gas of the at least one component gas may simply be accomplished by selecting the correct single component of a single component source gas.

While the above description describes preferred embodiments, it will be appreciated that these embodiments are susceptible to modification and change without departing from the scope of the invention and the fair meaning of the accompanying claims.

We claim:

1. An apparatus for inducing and maintaining a target end tidal gas concentration of a gas X in a subject, comprising:
   a) an inlet for at least one component gas of a source gas;
   b) a source gas outlet configured for connection to a partial re-breathing circuit; and
   c) means for controlling the end tidal concentration of the gas X based on the rate of flow of the source gas into the partial rebreathing circuit and the concentration of the gas X in the source gas using an algorithm in which:
      (i) the source gas outlet is assumed to be connected to a partial rebreathing circuit;
      (ii) the flow rate of the source gas into the partial rebreathing circuit is assumed to be less than the subject's minute ventilation; and
      (iii) the concentration of the gas X in the source gas is computed from:
         A) a target end tidal concentration of the gas X;

B) the flow rate of the source gas into the partial rebreathing circuit; and
C) if the gas X is a gas consumed by the patient, the minute consumption of the gas X, or if the gas X is a gas produced by the patient, the minute production of the gas X;
D) wherein if the gas X is a gas consumed by the patient, then the composition of the source gas is selected based on an algorithm derived from the following equation:

$$FG^1X = F_TETX + \frac{\dot{V}X}{\dot{V}G^1},$$

where $\dot{V}X$ is the subject's minute consumption of the gas X, $F_{T\!ET}X$ is the target end tidal concentration of the gas X, and $\dot{V}G^1$ is the flow rate of the source gas;
E) wherein if the gas X is a gas produced by the patient, then the composition of the source gas is selected based on an algorithm that is derived from the following equation:

$$FG^1X = F_TETX - \frac{\dot{V}X}{\dot{V}G^1},$$

where $\dot{V}X$ is the subject's minute production of the gas X, $F_{T\!ET}X$ is the target end tidal concentration of the gas X, and $\dot{V}G^1$ is the flow rate of the source gas.

2. The apparatus of claim 1, wherein the means for controlling the end tidal concentration, of the gas X is a processor unit programmed to control the end tidal concentration of the gas X independently of the end tidal concentration of other gases consumed or produced by the subject.

3. The apparatus of claim 2, wherein the processor unit is programmed to control the end tidal concentrations of carbon dioxide and oxygen independently of one another and independently of minute ventilation.

4. The apparatus of claim 3, wherein the processor unit is programmed to control end tidal concentrations of carbon dioxide and oxygen for a duration required to determine vascular reactivity.

5. The apparatus of claim 3, wherein the processor unit is programmed to standardize a carbon dioxide gas stimulus for magnetic resonance imaging of vascular reactivity.

6. The apparatus of claim 3, further comprising means for monitoring end tidal $CO_2$ and $O_2$ concentrations.

7. The apparatus of claim 6, further comprising means for monitoring pressure in the partial rebreathing circuit.

8. The apparatus of claim 3, wherein the patient's minute production of carbon dioxide and minute consumption of oxygen is estimated.

9. The apparatus of claim 3, wherein the processor unit is programmed to control end tidal concentrations of carbon dioxide and oxygen for a predetermined duration.

10. The apparatus of claim 2, wherein the gas flow into the partial rebreathing circuit comprises at least three component gases, and wherein the apparatus is programmed to maintain a targeted concentration of the gas X which is a constituent of at least one of the component gases.

11. The apparatus of claim 2, wherein the partial rebreathing circuit is a sequential gas delivery circuit.

12. The apparatus of claim 2, wherein the processor unit is configured to implement the algorithm with a machine readable code.

13. The apparatus of claim 2, wherein the apparatus is configured to be connected to an external processor unit.

14. The apparatus of claim 2, wherein the apparatus is sold with rights to program the processor with machine readable code that implements the algorithm.

15. The apparatus of claim 2, further comprising a non-transient storage medium encoded with a machine readable code that implements the algorithm when executed by the processor.

16. The apparatus of claim 1, wherein control of the composition of the source gas is achieved by using a plurality of pre-mixed component gases, each of the component gases containing oxygen.

17. The apparatus of claim 16, wherein the composition of the source gas is controlled by controlling the flow rate of the one or more component gases.

18. The apparatus of claim 17, wherein the at least three component gases include gas A, gas B, and gas C having the following relative concentrations: a) gas A: 50-100% $O_2$, 0-20% $CO_2$ b) gas B: 10-30% $O_2$, 20-80% $CO_2$, c) Gas C 10-30% $O_2$, 0-20% $CO_2$.

19. The apparatus of claim 16, wherein the flow rate of each component gas is controlled by a flow controller which receives input from a processor unit programmed to control the end tidal concentration of the gas X based on the algorithm.

20. The apparatus of claim 1, further comprising a non-transient storage medium encoded with instructions to download a machine readable code that implements the algorithm when executed by the processor.

21. The apparatus of, claim 1, wherein the algorithm employs an estimate of at least one of the subject's minute production of the gas X and the subject's consumption of the gas X.

* * * * *